United States Patent
Höland et al.

(10) Patent No.: US 6,200,137 B1
(45) Date of Patent: *Mar. 13, 2001

(54) CHEMICALLY STABLE TRANSLUCENT APATITE GLASS CERAMIC

(75) Inventors: Wolfram Höland; Martin Frank, both of Schaan (LI); Helga Drescher, Feldkirch (AT); Volker Rheinberger, Vaduz (LI)

(73) Assignee: Ivoclar AG (LI)

( * ) Notice: Subject to any disclaimer, the term of this patent is extended or adjusted under 35 U.S.C. 154(b) by 0 days.

This patent is subject to a terminal disclaimer.

(21) Appl. No.: 09/096,625

(22) Filed: Jun. 12, 1998

Related U.S. Application Data

(60) Provisional application No. 60/064,015, filed on Nov. 3, 1997.

(30) Foreign Application Priority Data

Jun. 12, 1997 (DE) ................................. 197 25 553

(51) Int. Cl.$^7$ ........................ A61C 13/083; C03C 10/16
(52) U.S. Cl. ................ 433/212.1; 428/432; 428/699; 428/701; 428/702; 65/21.2; 65/134.1; 427/2.29; 427/376.2; 501/3; 501/10; 501/32; 501/59; 501/67; 501/72
(58) Field of Search .......................... 428/689, 697, 428/699, 701, 702; 501/7, 57, 58, 59, 63, 66, 69, 70, 72, 67, 3, 10, 32; 106/35; 433/212.1, 208, 209; 65/21.2, 134.1; 427/2.29, 376.2

(56) References Cited

U.S. PATENT DOCUMENTS

| | | | |
|---|---|---|---|
| 4,101,330 | * 7/1978 | Burk et al. | 106/45 |
| 4,481,036 | * 11/1984 | Panzera | 106/35 |
| 4,536,480 | 8/1985 | Flannery et al. | 501/32 |
| 4,536,481 | 8/1985 | Flannery et al. | 501/32 |
| 4,551,099 | * 11/1985 | Panzera | 433/212.2 |
| 4,652,534 | * 3/1987 | Kasuga | 501/5 |
| 4,731,394 | * 3/1988 | Vogel et al. | 523/115 |
| 4,798,536 | * 1/1989 | Katz | 433/212.2 |
| 4,877,402 | 10/1989 | Hirabayashi et al. | 433/218 |
| 5,232,878 | 8/1993 | Kasuga et al. | 501/10 |
| 5,281,563 | * 1/1994 | Komma et al. | 501/59 |
| 5,318,929 | * 6/1994 | Jana et al. | 501/10 |
| 5,336,642 | * 8/1994 | Wolcott | 501/3 |
| 5,618,763 | * 4/1997 | Frank et al. | 501/5 |
| 5,698,019 | * 12/1997 | Frank et al. | 106/35 |

FOREIGN PATENT DOCUMENTS

| | | |
|---|---|---|
| 44 23 793 C1 | 2/1996 | (DE). |
| 44 28 839 A1 | 2/1996 | (DE). |
| 50-21015 | 3/1975 | (JP). |
| 63-176335 | 7/1988 | (JP). |
| 1093439 | 4/1989 | (JP). |

OTHER PUBLICATIONS

Clifford et al., "Apatite–Mullite Glass–Ceramics," *Journal of Non–Crystalline Solids* 196:346–351 (1996) (no month).

Hobo et al., "Castable Apatite Ceramics as a New Biocompatible Restorative Material," *Quintessence International* 2:135–141 (1985) (no month).

Taira et al., "Dental Cutting Behaviour of Mica–Based and Apatite–Based Machinable Glass–Ceramics," *J. Oral Rehabil.* 17:461–472 (1990) (no month).

Wakasa et al., "An Experimental Study of Dental Ceramic Material: Differential Thermal Analysis," *J. Mat. Sci. Lett.* 11:339–340 (1992) (no month).

* cited by examiner

*Primary Examiner*—Deborah Jones
*Assistant Examiner*—Stephen Stein
(74) *Attorney, Agent, or Firm*—Nixon Peabody LLP

(57) ABSTRACT

An apatite glass ceramic is described which is characterized by good chemical stability, a low expansion coefficient and high translucence, and is particularly suitable, by itself or together with glasses or other glass ceramics, as a veneering material for ceramic dental restorations.

21 Claims, No Drawings

CHEMICALLY STABLE TRANSLUCENT APATITE GLASS CERAMIC

This appln claims the benefit of U.S. Provisional No. 60/064,015 filed Nov. 3, 1997.

The invention relates to a chemically stable, translucent apatite glass ceramic which is particularly suitable for use in restorative dentistry and above all for coating or veneering of dental restorations, such as bridges or crowns.

Apatite glass ceramics are known from the prior art. They are usually employed as bioactive materials for replacing bone in human medicine, or as the main component of glass ionomer cements in dentistry.

In the case of bioactive materials for bone replacement, they have very high CaO and $P_2O_5$ contents, however, in order to achieve bioactivity, i.e. the direct growing together of glass ceramic and living bone.

A glass ceramic implantation material is known from DE-A-40 20 893 which has apatite crystals but also contains very large quantities of CaO in order to achieve bioactivity.

Glass ceramics for glass ionomer cements also have high CaO contents and mostly also high fluoride ion contents, in order to obtain the desired high level of ion release in the oral medium.

These two types of apatite glass ceramics are white-opaque, however, and have a high level of ion release and/or bioactivity, so they are not suitable for restorative dentistry.

An apatite glass ceramic for restorative dentistry must have optical properties such as translucence and colour which are similar to those of the natural tooth. A material which is impervious to light, i.e. opaque, is not suitable for this purpose. Moreover, bioactivity or a high level of ion release is undesirable; rather, a high degree of chemical stability is required which should even exceed that of the natural tooth.

In known apatite-containing glass ceramics for restorative dentistry, the main crystal phase is regularly formed not by apatite but by leucite or mullite. This is undesirable, however, since these types of crystals make it difficult, inter alia to imitate the optical properties of the natural tooth material composed primarily of needle-shaped apatite.

EP-A-0 690 030 discloses leucite-containing phospho-silicate glass ceramics which may be used in dental engineering. In view of the leucite content, however, they have very high thermal expansion coefficients so they are not -suitable for the coating of materials with low expansion coefficients, such as lithium disilicate glass ceramics.

Moreover, an apatite glass ceramic containing mullite as a further crystal phase is described by A. Clifford and R. Hill (Journal of Non-Crystalline Solids 196 (1996) 346–351). The high mullite content brings about only low translucence.

Apatite-containing glass ceramics are disclosed by S. Hobo et al. (Quintessence International 2 (1985) 135–141) and Wakasa et al. (J. Oral Rehabil. 17 (1990) 461–472 and J. Mat. Sci. Lett. 11 (1992) 339–340) for restorative tooth replacement. Said glass ceramics have high CaO and $P_2O_5$ contents, however, so they show only poor chemical stability. Moreover, the apatite crystals in these glass ceramics do not have a needle-shaped morphology.

Moreover, DE-A-34 35 348 describes apatite-containing glass ceramics for the production of dental crowns. The glass ceramics, however, contain no $Al_2O_3$ at all and very large quantities of CaO, for which reason they have a high tendency to ion exchange and consequently only poor chemical stability. In addition, the apatite crystals do not have the needle-shaped morphology which is characteristic of apatite crystals of natural tooth material.

Glass ceramics with good chemical stability are disclosed in EP-A-0 695 726 as alkali-zinc-silicate glass ceramics. The disadvantage of said glass ceramics, however, is that they contain leucite rather than apatite as the crystal phase. As a result of the high expansion coefficient of leucite, the glass ceramics are therefore usually unsuitable as coatings for substrates with low expansion coefficients, such as, in particular, lithium disilicate glass ceramics. The glass ceramic also necessarily contains ZnO in order to achieve good chemical stability.

The object of the invention, therefore, is to provide an apatite glass ceramic which resembles natural tooth material in terms of its optical properties and, in particular, its high translucence, and contains apatite crystals which have a greater chemical stability than the carbonate-apatite crystals of natural tooth material and hence confer excellent chemical stability on the glass ceramic. Moreover, the apatite glass ceramic should preferably contain apatite crystals with a similar morphology to that of the apatite crystals of natural tooth material and have a low thermal expansion coefficient and should therefore be particularly suitable as a dental material and above all as a coating or veneer for dental restorations, such as crowns or bridges, made of lithium disilicate.

Surprisingly, said object is achieved by the chemically stable, translucent apatite glass ceramic according to the present invention.

The invention also provides the process for the production of the apatite glass ceramic, a dental material as well as dental uses and shaped dental products.

The apatite glass ceramic according to the invention is characterised in that it contains CaO, $P_2O_5$ and F in a molar ratio of:

$CaO:P_2O_5:F$ 1:0.020 to 1.5:0.03 to 4.2 and contains apatite crystals as the main crystal phase.

The molar ratio of $CaO:P_2O_5:F$ in the glass ceramic is preferably 1:0.1 to 0.5:0.1 to 1.0 since this leads to particularly stable glass ceramics.

Surprisingly, it has become apparent that by adjusting the molar ratio of CaO to $P_2O_5$ to F in the stated manner, apatite glass ceramics are obtained which show an increased chemical stability compared with conventional apatite glass ceramics.

In order to quantify the chemical stability, the test method according to ISO specification 6872:1995 described for glass ceramics was carried out, in which the resistance to aqueous acetic acid solution is determined by measuring the loss of mass in $\mu g/cm^2$ that occurs. The essential stages of this method are given in the Examples.

The apatite glass ceramic according to the invention usually exhibits a loss of mass of less than 200 and preferably less than 100 $\mu g/cm^2$. Particularly preferred glass ceramics have a loss of mass of less than 60 $\mu g/cm^2$.

Advantageous apatite glass ceramic according to the invention is also characterised in that it contains at least one of the following components:

| Component | Wt. % |
|---|---|
| $SiO_2$ | 45.0 to 70.0 |
| $Al_2O_3$ | 5.0 to 22.0 |
| $P_2O_5$ | 0.5 to 6.5 |
| $K_2O$ | 3.0 to 8.5 |
| $Na_2O$ | 4.0 to 13.0 |

-continued

| Component | Wt. % |
|---|---|
| CaO | 1.5 to 11.0 |
| F | 0.1 to 2.5 |

The glass ceramic according to the invention may additionally contain at least one of the following components:

| Component | Wt. % |
|---|---|
| $B_2O_3$ | 0 to 8.0 |
| $La_2O_3$ | 0 to 5.0 |
| $Li_2O$ | 0 to 5.0 |
| BaO | 0 to 5.0 |
| MgO | 0 to 5.0 |
| ZnO | 0 to 5.0 |
| SrO | 0 to 7.0 |
| $TiO_2$ | 0 to 4.0 |
| $ZrO_2$ | 0 to 4.0 |
| $CeO_2$ | 0 to 3.0 |

The lower limits for those additional components are usually 0.05 wt. %.

Preferred quantity ranges exist for the individual components of the apatite glass ceramic according to the invention. Unless otherwise specified, these may be chosen independently of one another and are as follows:

| Component | Wt. % |
|---|---|
| $SiO_2$ | 50.0 to 68.0 |
| $Al_2O_3$ | 7.0 to 21.0 |
| $P_2O_5$ | 0.5 to 4.0 |
| $K_2O$ | 4.0 to 8.0 |
| $Na_2O$ | 4.0 to 11.0 |
| CaO | 2.0 to 8.0 |
| F | 0.2 to 2.0 |
| $B_2O_3$ | 0.2 to 4.0 |
| $La_2O_3$ | 0 to 3.0 |
| $Li_2O$ | 0 to 3.0 |
| BaO | 0 to 4.0 |
| MgO | 0 to 4.0 |
| ZnO | 0 to 4.0 |
| SrO | 0 to 5.0 |
| $TiO_2 + ZrO_2$ | 0.2 to 5.0 |
| $CeO_2$ | 0 to 2.0 |

Particularly preferred quantity ranges for the individual components of the apatite glass ceramic according to the invention are as follows and these may be chosen independently of one another:

| Component | Wt. % |
|---|---|
| $SiO_2$ | 54.0 to 65.0 |
| $Al_2O_3$ | 8.0 to 21.0 |
| $P_2O_5$ | 0.5 to 3.5 |
| $K_2O$ | 5.0 to 8.0 |
| $Na_2O$ | 6.0 to 11.0 |
| CaO | 2.0 to 6.0 |
| F | 0.3 to 1.5 |
| $B_2O_3$ | 0.2 to 3.0 |
| $La_2O_3$ | 0 to 2.0 |
| $Li_2O$ | 0 to 2.0 |
| BaO | 0 to 3.0 |
| MgO | 0 to 3.0 |

-continued

| Component | Wt. % |
|---|---|
| ZnO | 0 to 3.0 |
| SrO | 0 to 4.0 |
| $TiO_2$ | 0.5 to 2.0 |
| $ZrO_2$ | 0.5 to 3.0 |
| $CeO_2$ | 0.1 to 1.5 |

All the above-mentioned quantities in wt. % relate to the glass ceramic.

The glass ceramic according to the invention may also contain e.g. conventional colour components for matching the colour of a patient's natural tooth material.

It was ascertained by scanning electron microscope and X-ray diffraction analyses that apatite, such as hydroxy and/or fluoroapatite, forms the main crystal phase in the glass ceramic. The apatite crystals are preferably hexagonal and in particular needle-shaped. The apatite crystals are preferably smaller than 35 μm in their greatest extension, particularly smaller than 15 μm, and in particular preference smaller than 5 μm.

The optical properties of the glass ceramic are controlled by means of the precipitated apatite crystals which preferably resemble the carbonate-apatite crystals of natural tooth material in terms of their appearance. It is thus possible to produce a glass ceramic with an appearance which corresponds to that of the dentine or enamel of the tooth. At the same time, an optical depth is achieved in the glass ceramic which is not possible by means of other types of crystals.

The glass ceramic according to the invention is characterised not only by very good chemical stability but also by translucence. In order to quantify the translucence, the CR value was determined according to the method described in the Examples. The CR value, also known as the contrast ratio, indicates the ratio of light reflection of a specimen of the glass ceramic on a black background to the measurement of the light reflection of the specimen on a white background, and thus serves as a measure of the translucence of a material. The CR value is defined by the following formula:

$$CR = Y_b/Y_w$$

where

CR=contrast ratio $Y_b$=light reflection of the specimen on a black background, and $Y_w$=light reflection of the specimen on a white background.

The CR value always lies in the range from 0 to 1, where CR=0 stands for an opacity of 0% and consequently a completely translucent material, and CR=1 stands for an opacity of 100% and consequently a completely opaque material, i.e. one which is impervious to light.

The glass ceramic according to the invention usually has a CR value of 0 to 0.9 and preferably 0.1 to 0.75.

A further particular advantage of the glass ceramic according to the invention is that, due to its particular molar ratio of CaO to $P_2O_5$ to F in combination with the precipitated apatite crystals, good chemical stability is achieved without ZnO necessarily having to be present.

It is presumed that this stability is also attributable to the very high degree of crystallinity and to the preferential formation of hydroxy and fluoroapatite. The stability of the precipitated fluoro or hydroxyapatite crystals is higher than that of the rather unstable carbonate-apatite, which is present in natural tooth material.

It should also be pointed out that the glass ceramic may be produced in the $B_2O_3$-free form. The advantage of adding $B_2O_3$, however, is that the entire sintering behaviour of the glass ceramic is improved and sintering can take place in the preferred temperature range of 650° C. to 1050° C.

The apatite glass ceramic usually has a very low thermal expansion coefficient of 6.0 to $12.0 \times 10^{-6} K^{-1}$, measured in the temperature range from 100° C. to 400° C.

In order to produce the apatite glass ceramic according to the invention,
- a) a starting glass containing the necessary components is melted at temperatures of 1200° C. to 1650° C.,
- b) the glass melt obtained is poured into water with the formation of glass granules,
- c) the glass granules are optionally comminuted to a glass powder with an average particle size of 1 to 450 μm, based on the number of particles, and
- d) the glass granules or glass powder is subjected to a heat treatment at temperatures of more than 900° C. and up to 1200° C. for a period of 30 minutes to 6 hours.

In stage (a), a starting glass is first melted by intimately mixing suitable starting materials, such as carbonates, oxides and fluorides, and heating them to the given temperature.

In stage (b), the glass melt obtained is then quenched by being poured into water and is thereby converted to glass granules. This procedure is usually also referred to as fritting.

Optionally, the glass granules are then comminuted in stage (c) and ground, particularly with conventional mills, to the desired particle size. The glass powder obtained preferably has an average particle size of 1 to 450 μm, based on the number of particles.

In stage (d), the glass granules or optionally the glass powder undergo a heat treatment at temperatures of more than 900° C. to 1200° C. for a period of 30 minutes to 6 hours, preferably 30 minutes to 3 hours. A temperature of more than 900° C. is required since the development of the apatite crystals in the desired form and quantity does not take place at lower temperatures.

Volume crystallisation takes place during the heat treatment. This leads to a homogeneous distribution of the apatite crystals throughout the glass ceramic, in contrast to leucite-crystallisation, which can only occur on the internal surfaces of a glass powder.

The process of glass fritting described in stage (b) is responsible for freezing a glass structure with very small (<100 nm) droplet-shaped precipitates which are extremely densely packed and finely distributed. Even under the scanning electron microscope with a 30,000 fold magnification, a residual glass matrix can no longer be detected. It is assumed that the apatite crystallisation taking place during the subsequent heat treatment proceeds via these precipitates which can therefore be regarded as primary nuclei.

It was ascertained by scanning electron microscopy and X-ray diffraction analyses that apatite, preferably fluoroapatite, forms the main crystal phase. The size of the crystals obtained can be controlled by the temperature selected and the duration of the heat treatment. In addition to the apatite crystals, further crystal phases may be formed depending on the chemical composition of the starting glass used. In addition to the various crystal phases, microheterogeneous demixing regions, i.e. various glass phases, may also be present. These regions can be identified under the scanning electron microscope as small microheterogeneous droplet glass phases about 20 to 400 nm in size. The droplet glass phases occurring, together with the crystals, influence the optical properties of the glass ceramics according to the invention, such as opalescence and translucence.

Surprisingly, the optical properties of the apatite glass ceramic according to the invention may be adjusted from glassy transparent to whitish cloudy. This is absolutely vital for use as dental material or component thereof in order to be able to produce all the various forms of the natural tooth in a reproducible manner. The fine apatite crystals in the microstructure of the glass ceramic preferred according to the invention bring about a very great similarity to the natural tooth in terms of optical appearance and structure.

The apatite glass ceramic according to the invention is therefore used particularly as a dental material and preferably as a component of dental material.

When apatite glass ceramic is used as a component of dental material, it is possible, by a suitable choice of its composition and of the type of other components, to obtain dental materials with good chemical stability in which important properties, such as processing temperature, optical properties and thermal expansion coefficient, are matched exactly to the respective requirements. This is often not possible with pure glass ceramic.

A combination of the desired properties may be obtained with the apatite glass ceramic according to the invention by mixing it with glasses and/or other glass ceramics. It is preferable in this case that the dental material contains 10 to 90 wt. % of the apatite glass ceramic.

It is in particular possible to use the glass ceramic according to the invention as a means to modify the optical properties of glasses and other glass ceramics. In case of a dental ceramic it is a goal to achieve balance between translucence and lightness, which closely resembles the natural teeth. A satisfactory dental restoration must simultaneously have a bright appearance and a high translucence.

Upon use of conventional opacifiers, such as $SnO_2$, this cannot be obtained. If the lightness is satisfactory, then the translucence is too low to match the properties of natural teeth.

By using the apatite glass-ceramic according to the invention as opacifier having cristalls of a size of generally up to 15 μm and particularly up to 5 μm a lightness and translucence similar to that of natural teeth can surprisingly be obtained.

The dental material according to the invention preferably contains, in addition to the apatite glass ceramic, at least one glass and/or glass ceramic of the systems comprising alkali-silicate, alkali-alkaline earth silicate, alkali-aluminosilicate, alkali-zinc-borosilicate, phosphosilicate or alumino-fluoro-borosilicate. Preferred glass ceramics and glasses of this kind are given below, the details in wt. % relating to the glass ceramic in question or the glass in question.

Leucite-containing phosphosilicate glass ceramic having the composition:
$SiO_2$ 49.0–57.5 wt. %, $Al_2O_3$ 11.4–21.0 wt. %, $P_2O_5$ 0.5–5.5 wt. %, CaO 2.5–11.5 wt. %, $K_2O$ 9.0–22.5 wt. %, $Na_2O$ 1.0–9.5 wt. %, $Li_2O$ 0–2.5 wt. %, $B_2O_3$ 0–2.0 wt. %, $TiO_2$ 0–3.0 wt. %, $ZrO_2$ 0.8–8.5 wt. %, $CeO_2$ 0–3.0 wt. %, F 0.25–2.5 wt. %, $La_2O_3$ 0–3.0 wt. %, ZnO 0–3.0 wt. %, BaO 0–3.0 wt. %, MgO 0–3.0 wt. % and SrO 0–3.0 wt. %.

Opalescent glasses having the composition:
$SiO_2$ 48.0–66.0 wt. %, $B_2O_3$ 0–1.0 wt. %, $Me(III)_2O_3$ 5.8–20.0 wt. %, $Me(I)_2O$ 6.0–22.0 wt. %, Me(II)O 3.5–16.0 wt. %, $Me(IV)O_2$ 0.5–10.0 wt. %, $P_2O_5$ 0.5–5.0 wt. %, $CeO_2$ 0–3.0 wt. %, wherein the quantity of $Me(III)_2O_3$ is formed by 5.8–20.0 wt. % of $Al_2O_3$ and 0–6.0 wt. % of $La_2O_3$; the quantity of $Me(I)_2O$ is formed by 3.0–15.0 wt. % of $K_2O$, 3.0–12.0 wt. % of $Na_2O$ and 0–2.5 wt. % of $Li_2O$; the quantity of $Me(II)O$ is formed by 0–10.0 wt. % of CaO, 0–7.5 wt. % of BaO, 0–9.0 wt. % of MgO, 0–3.5 wt. % of ZnO and 0–8.5 wt. % of SrO; and the quantity of $Me(IV)O_2$ is formed by 0–5.0 wt. % of $TiO_2$ and 0–5.0 wt. % of $ZrO_2$.

Alkali-zinc-silicate glasses having the composition: $SiO_2$ 52.0–63.5 wt. %, $Me(III)_2O_3$ 8.5–13.0 wt. %, $K_2O$ 0–20.5 wt. %, $Na_2O$ 1.5–20.0 wt. %, $Li_2O$ 0–5.0 wt. %, ZnO 2.0–8.0 wt. %, $Me(II)O$ 2.5–6.5 wt. %, $TiO_2+ZrO_2$ 0.5–6.0 wt. %, $SnO_2$ 0–9.5 wt. %, $P_2O_5$ 0–4.0 wt. %, F 0–2.0 wt. %, $CeO_2$ 0–3.0 wt. %, wherein the quantity of $Me(III)_2O_3$ is formed by 0–13 wt. % of $Al_2O_3$ and 0–9.5 wt. % of $La_2O_3$; and the quantity of $Me(II)O$ is formed by 0–3.5 wt. % of CaO, 0–4.5 wt. % of BaO and 0–5.0 wt. % of MgO.

In particular preference, however, at least one alkali silicate glass which can be produced by conventional methods having the following composition 55.0–71.0 wt. % of $SiO_2$, 5.0–16.0 wt. % of $Al_2O_3$, 0.2–10.0 wt. % of $B_2O_3$, 4.5–10.0 wt. % of $K_2O$, 3.0–14.0 wt. % of $Na_2O$, 0–4.0 wt. % of $Li_2O$, 0–3.0 wt. % of CaO, 0–5.0 wt. % of BaO, 0–4.0 wt. % of ZnO, 0.2–5.0 wt. % of $ZrO_2+TiO2$, 0–2.0 wt. % of $CeO_2$, 0–3.0 wt. % of F and 0–0.6 wt. % of $P_2O_5$ is used together with the apatite glass ceramic. The wt. % details are based on the glass. Mixtures of the apatite glass ceramic with at least one glass of this composition produce dental materials which are particularly suitable as coatings for ceramic frameworks and hence for the production of fully ceramic dental products with tooth-like optical properties and good chemical stability.

It is preferred to use glasses which do not crystallise during further processing of the dental material to dental products and particularly during sintering or other heating to 600° C. to 1000° C. for up to 2 h. Glasses having a sintering temperature from 650° C. to 1050° C. are advantageous.

The dental material according to the invention is used preferably for coating a substrate, particularly a dental crown or bridge. In particular, the dental material is sintered on to obtain the desired coating.

If used as a coating or veneering material, the apatite glass ceramic is usually comminuted initially to a powder with an average particle size of 5 to 80 μm, based on the number of particles. Additives such as colour components and in particular glasses or further glass ceramics, and aqueous solutions for mixing or modelling, are optionally added to said powder, and the mixture obtained is applied to the substrate and shaped in the desired manner. After shaping, sintering finally takes place at temperatures of 650° C. to 1050° C. to obtain the coated, shaped dental product.

It is also possible, however, to bond a dental restoration produced from the glass ceramic according to the invention to a substrate.

The apatite glass ceramic according to the invention may be used as a coating or veneering material for glass ceramic, all-ceramic or metallic dental frameworks or those based on a composite material, with a thermal expansion coefficient of 7.0 to 12.0, particularly 8.0 to $11.0 \times 10^{-6} K^{-1}$. It is used preferably for coating or veneering of $ZrO_2$ ceramics, $Al_2O_3$ ceramics, $ZrO_2/Al_2O_3$ ceramics, ceramic or glass ceramic composite materials and titanium.

It is used particularly advantageously, however, for veneering frameworks based on lithium disilicate glass ceramic in order to produce in this way aesthetically very attractive solid ceramic dental products which not only have excellent chemical stability but are also characterised by very high strength.

Lithium disilicate glass ceramics which have proved to be particularly suitable and were obtained by melting corresponding starting glasses, fritting and heat treatment at 400° C. to 1100° C. have the following composition:

| Component | Wt. % |
| --- | --- |
| $SiO_2$ | 57.0 to 80.0 |
| $Al_2O_3$ | 0 to 5.0 |
| $La_2O_3$ | 0.1 to 6.0 |
| MgO | 0 to 5.0 |
| ZnO | 0 to 8.0 |
| $K_2O$ | 0 to 13.5 |
| $Li_2O$ | 11.0 to 19.0 |
| $P_2O_5$ | 0 to 11.0 | with the proviso that (a) $Al_2O_3+La_2O_3$ is 0.1 to 7.0 wt. % and (b) MgO+ZnO is 0.1 to 9.0 wt. %.

For the production of coatings, dental material according to the invention having a thermal expansion coefficient that is smaller than that of the substrate to be coated is advantageous. Dental materials whose expansion coefficient is not more than $3.0 \times 10^{-6} K^{-1}$ smaller than that of the substrate are particularly advantageous. The dental material preferably has a linear thermal expansion coefficient of 5.5 to $12.5 \times 10^{-6} K^{-1}$, measured at temperatures from 100° C. to 400° C.

The apatite glass ceramic and the dental material according to the invention may be processed in the usual way together with the additives optionally present to obtain shaped dental products. Suitable shaped dental products according to the invention containing the apatite glass ceramic according to the invention or the dental material according to the invention are, apart from compacts of the desired shape or ingots, particularly dental restorations such as an inlay, an onlay, a bridge, an abutment, a jacket, a veneer, a facet, a filling, a connector, a crown or a partial crown.

Preferred apatite glass ceramic according to the invention contains no leucite since, as a result of its high thermal expansion coefficient, it would also confer a high thermal expansion coefficient of usually more than $12.5 \times 10^{-6} K^{-1}$ on the glass ceramic. If leucite-containing glass ceramic is used to coat a substrate that has an expansion coefficient of less than $12.5 \times 10^{-6} K^{-1}$, such as $ZrO_2$ or lithium disilicate glass ceramic, very high tensions are therefore also induced which result in cracks and detachments.

The invention is explained in more detail below on the basis of examples.

EXAMPLES

Example 1 to 17

A total of 17 different glass ceramics according to the invention were produced. They had the chemical compositions and molar ratios of CaO to $P_2O_5$ to F given in Table I and they all had a chemical stability of less than 100 μg/cm² loss of mass according to ISO 6872:1995.

TABLE 1

Composition of glass ceramics according to the invention (quantities in wt. %) and respective molar ratio CaO:P$_2$O$_5$:F

| Ex. No. | SiO$_2$ | Al$_2$O$_3$ | P$_2$O$_5$ | CaO | F | K$_2$O | Na$_2$O | Li$_2$O | B$_2$O$_3$ | TiO$_2$ | ZrO$_2$ | CeO$_2$ | BaO | ZnO | SrO | Molar ratio CaO:P$_2$O$_5$:F |
|---|---|---|---|---|---|---|---|---|---|---|---|---|---|---|---|---|
| 1 | 64.5 | 8.4 | 1.1 | 2.8 | 0.7 | 6.6 | 9.6 | — | 2.2 | 1.2 | 0.4 | — | — | 2.5 | — | 1:0.156:0.719 |
| 2 | 56.9 | 19.7 | 2.6 | 1.7 | 2.5 | 8.0 | 8.6 | — | — | — | — | — | — | — | — | 1:0.6:4.2 |
| 3 | 45.2 | 21.9 | 3.2 | 4.5 | 0.6 | 7.5 | 13.0 | 0.4 | 2.0 | 0.5 | 0.7 | 0.5 | — | — | — | 1:0.282:0.4 |
| 4 | 54.7 | 19.5 | 1.2 | 2.6 | 0.6 | 6.2 | 10.0 | — | 2.0 | 1.0 | 1.7 | 0.5 | — | — | — | 1:0.172:0.641 |
| 5 | 62.0 | 9.0 | 2.6 | 4.3 | 0.6 | 7.5 | 8.6 | — | — | 0.4 | 1.1 | 0.8 | — | — | 3.1 | 1:0.24:0.42 |
| 6 | 64.4 | 6.3 | 1.2 | 2.8 | 0.6 | 6.5 | 9.8 | — | — | 1.6 | 0.8 | 0.5 | 2.4 | 3.1 | — | 1:0.172:0.656 |
| 7 | 69.7 | 5.1 | 3.7 | 5.3. | 0.8 | 3.2 | 4.1 | 5.0 | 0.9 | 0.8 | 0.8 | 0.6 | — | — | — | 1:0.277:0.429 |
| 8 | 62.8 | 13.1 | 1.2 | 2.7 | 0.6 | 6.3 | 5.9 | — | — | — | 1.7 | 0.5 | 1.8 | 3.4 | — | 1:0.172:0.641 |
| 9 | 55.5 | 19.2 | 1.2 | 2.7 | 0.6 | 6.7 | 9.7 | — | 0.3 | 1.4 | 2.2 | 0.5 | — | — | — | 1:0167:0.621 |
| 10 | 53.7 | 13.7 | 2.6 | 11.2 | 0.12 | 8.3 | 7.9 | 0.58 | — | 0.7 | 0.7 | 0.5 | — | — | — | 1:0.086:0.032 |
| 11 | 55.5 | 9.8 | 2.8 | 4.9 | 1.5 | 5.7 | 3.8 | 0.2 | 8.0 | 1.3 | 1.1 | 0.5 | 2.8 | 2.1 | — | 1:0.224:0.897 |
| 12 | 55.4 | 19.9 | 0.5 | 2.0 | 0.4 | 7.4 | 7.3 | — | — | — | 1.6 | 0.7 | 4.8 | — | — | 1:0.096:0.6 |
| 13 | 57.5 | 8.0 | 3.1 | 5.1 | 1.7 | 6.6 | 9.2 | — | 3.3 | 1.3 | 0.8 | 0.8 | — | 2.6 | — | 1:0.241:1 |
| 14 | 59.2 | 7.9 | 3.0 | 5.1 | 0.6 | 6.8 | 9.6 | 0.3 | 1.0 | 1.5 | 2.5 | 0.5 | — | 2.0 | — | 1:0.233:0.35 |
| 15 | 54.4 | 19.5 | 2.6 | 1.7 | 2.5 | 7.9 | 8.6 | 0.4 | 0.4 | 0.7 | 0.8 | 0.5 | — | — | — | 1:0.6:4.2 |
| 16 | 54.3 | 18.4 | 6.4 | 1.7 | 2.4 | 7.8 | 7.5 | 0.4 | 0.4 | 0.7 | — | — | — | — | — | 1:1.485:4.16 |
| 17 | 50.1 | 18.2 | 0.6 | 10.9 | 0.15 | 7.7 | 8.5 | 0.7 | — | 0.7 | 0.7 | 0.55 | — | 1.2 | — | 1:0.021:0.04 |

In order to produce said glass ceramics, an appropriate batch of suitable oxides, carbonates and fluorides in each case was melted in a platinum/rhodium crucible at a temperature of 1550° C. to 1600° C. for a homogenisation period of 1 to 1.5 hours. The glass melt was quenched in water, and the granules of starting glass formed were dried and ground to an average particle size of less than 90 μm.

The powder of starting glass obtained then underwent a heat treatment at more than 900° C. and up to 1200° C. for 30 minutes to 6 hours, whereupon the glass ceramic formed.

Selected properties that were determined on specimens of the respective glass ceramic are given in Table II for some of the glass ceramics. Moreover, details about the heat treatment actually chosen for the starting glass are given in Table II under "Heat treatment".

The examples illustrate how, by altering the chemical composition, glass ceramics with differing processing properties and optical properties but always having good chemical stability can be obtained.

TABLE II

| Ex. | Heat treatment [° C./h] | Firing temperature [° C.] | Tg [° C.] | α-value × 10$^{-6}$K$^{-1}$ (100° C.– 400° C.) | Optical appearance | Acid resistance [μg/cm$^2$] |
|---|---|---|---|---|---|---|
| 1 | 1050/1 | 860 | 545 | 8.4 | milky, slightly opal, translucent | 21 |
| 8 | 1000/1 | 1080 | 650 | 7.9 | very translucent | 23 |
| 9 | 1020/1 | 1050 | 645 | 9.7 | very translucent | 28 |
| 11 | 1000/1 | 890 | 547 | 6.6 | yellowish, milky, translucent | 58 |
| 14 | 1050/1 | 870 | 541 | 9.4 | whitish, cloudy, translucent | 55 |

*Firing temperature = temperature which was used during production of the specimens by sintering onto quartz (1 minute: holding time, vacuum)

Determination of the expansion coefficient α

In order to measure the thermal expansion coefficient α, a rod-shaped green compact was prepared from powder of the glass ceramic in question, and said compact was sintered in a vacuum furnace at a rate of heating of 60° C./min and with a holding time of 1 minute at the sintering temperature given in each case. A glaze bake was then carried out without vacuum at a 20° C. higher final temperature and with a holding time of 1 minute. The thermal expansion coefficient was determined on the specimen obtained.

Determination of acid resistance

The acid resistance is a measure of the chemical stability of glass ceramics used in the dentistry, since these are permanently exposed to the action of acid substances in the oral cavity.

The acid resistance was determined according to the ISO specification 6872:1995. To this end, small sample plates 12 mm in diameter and 1 mm thick were prepared initially by sintering together glass ceramic granules with an average particle size of 90 μm. The granules were kept at the sintering temperature for 1 minute. The sample plates were then treated for 16 hours in a Soxhlet apparatus with 4 vol. % of aqueous acetic acid and finally the loss of mass occurring was determined as a measure of the acid resistance.

Mixtures of the apatite glass ceramics with additional components were examined in the following examples. Glasses and/or other glass ceramics which were used as additional components had the composition given in Table III.

TABLE III

Composition of glasses and glass ceramics as additional components
(details in wt. %)

| Add. component | SiO$_2$ | Al$_2$O$_3$ | P$_2$O$_5$ | CaO | F | K$_2$O | Na$_2$O | Li$_2$O | B$_2$O$_3$ | TiO$_2$ | ZrO$_2$ | CeO$_2$ | BaO | ZnO |
|---|---|---|---|---|---|---|---|---|---|---|---|---|---|---|
| Alkali silicate glass (A) | 61.5 | 8.7 | — | 1.0 | 1.7 | 7.0 | 8.8 | — | 2.4 | 1.5 | 1.0 | 0.5 | 2.9 | 3.0 |
| Alkali silicate glass (B) | 61.4 | 8.5 | — | 1.1 | 1.7 | 7.8 | 8:7 | 0.6 | 1.9 | 1.5 | 1.0 | 0.5 | 2.1 | 3.2 |
| Alkali silicate glass (C) | 62.3 | 8.7 | — | 1.3 | 1.6 | 7.0 | 7.0 | 2.0 | 1.1 | 1.4 | 1.0 | 0.6 | 3.0 | 3.0 |
| Alkali silicate glass (D) | 70.8 | 8.6 | — | 2.1 | 0.9 | 6.9 | 8.3 | 1.5 | 0.2 | 0.7 | — | — | — | — |
| Alkali silicate glass (E) | 63.4 | 6.2 | 0.4 | 1.7 | — | 6.4 | 9.6 | — | 3.7 | 1.7 | 1.1 | 0.5 | 2.3 | 3.0 |
| Alkali silicate glass (F) | 61.9 | 9.9 | — | 1.1 | 1.5 | 5.8 | 3.7 | 0.2 | 8.0 | 1.4 | 1.1 | 0.5 | 2.8 | 2.1 |
| Leucite phosphosilicate glass ceramic (G) | 56.8 | 13.6 | 2.6 | 3.7 | 0.3 | 10.8 | 7.5 | 0.2 | 0.3 | 0.4 | 1.1 | 1.0 | 0.9 | 0.8 |
| Alkali zinc silicate glass (H) | 57.1 | 9.5 | — | 1.9 | 0.9 | 9.6 | 9.3 | 1.7 | — | — | 1.0 | 1.0 | 3.9 | 4.1 |
| Opalescent glass (I) | 55.8 | 15.2 | 2.6 | 2.6 | — | 11.0 | 9.6 | — | 0.3 | — | 1.9 | 1.0 | — | — |

Example 18

This Example describes the use of the glass ceramic according to the invention according to Example 9 as a coating material for ceramic frameworks and thus for the production of all-ceramic dental products.

Glass powder of the appropriate composition was heat treated for 1 hour at 1020° C. for the production of the glass ceramic. The glass ceramic formed was examined by scanning electron microscopy and the crystals formed could be identified by X-ray diffractometry as needle-shaped apatite crystals.

In order to obtain a suitable expansion coefficient and sintering temperature, the glass ceramic was mixed with the alkali silicate glasses (A) and (B) (see Table III).

The production of these alkali silicate glasses took place in a manner similar to the production of the starting glasses described above in Examples 1 to 17.

The glass ceramic and the two alkali silicate glasses were mixed in the form of powders having an average particle size of less than 90 μm and in a weight ratio of 40% apatite glass ceramic according to Example 9 (see Table II), 30% alkali silicate glass (A) and 30% alkali silicate glass (B).

This mixture was sintered at 870° C. to a rod-shaped green compact in a vacuum furnace at a rate of heating of 60° C./min and with a holding time of 1 min. A thermal expansion coefficient of $9.5 \times 10^{-6} K^{-1}$, measured in the temperature range of from 100 to 400° C., was determined for the sample obtained.

This mixture could thus be used for sintering on to a substrate with a thermal expansion coefficient of $10.6 \times 10^{-6} K^{-1}$, such as lithium disilicate glass ceramic, at an advantageous processing temperature of 830° C. This processing on the tooth substrate can usually take place at temperatures that are 50° C. to 100° C. lower than for sintering onto quartz.

The fully ceramic products obtained are characterised by good chemical stability, an aesthetic appearance and high strength.

Example 19

In the same way as Example 18, different apatite glass ceramics according to the invention may also be mixed together or with other glasses to obtain desired expansion coefficients and sintering temperatures.

A powder mixture of 25 wt. % of glass ceramic according to Example 4 (heat treatment at 1020° C.), 50 wt. % of glass ceramic according to Example 14 (heat treatment at 1050° C.) and 25 wt. % of alkali silicate glass (B) (see Table III.)

was produced. This mixture had an advantageous sintering temperature of only 830° C. and an expansion coefficient of $9.5 \times 10^{-6} K^{-1}$.

The mixture had good chemical stability and outstanding optical properties and was highly suitable as a sintering ceramic for an all-ceramic dental framework with a low expansion coefficient.

Example 20 to 27

Further mixtures of apatite glass ceramics according to the invention with glasses and glass ceramics were examined in these Examples.

The compositions of the individual mixtures and the heat treatment carried out for the production of the apatite glass ceramic used in each case are listed in Table IV.

The properties determined for these mixtures are also give in Table IV, and they show that it is possible, by means of a suitable choice of components, to obtain dental materials with properties matched to the application in question which in any event are-characterised by good chemical stability.

The specimens were placed in the designated opening in a Minolta-CR 300 colour measuring instrument and the reflection of each of the 5 specimens was measured with an aperture of 10 mm. The samples must not be in optical contact with the background during the measurement, a situation which may be prevented if necessary by applying a drop of glycerol onto the background.

(a) In order to determine the sample emission on a black background $Y_b$ ($Y_{black}$), a black plate with not more than 4% reflection was used.

(b) In order to determine the sample emission on a white background $Y_w$ ($Y_{white}$), a white plate with a reflection of 80 to 85% was used.

The contrast value CR was then calculated from the $Y_b$ and $Y_w$ values determined according to $CR=Y_b/Y_w$, and it was as follows for the two materials examined:

Material 1: $CR_1=0.13 \rightarrow 13\%$ opacity

Material 2: $CR_2=0.50 \rightarrow 50\%$ opacity

The materials had the following composition:

Material 1: Composition like the mixture according to Example 20

TABLE IV

Compositions and properties of mixtures of apatite glass ceramics according to the invention with glasses and/or glass ceramics

| Ex. | Composition | Heat treatment [° C./h] | Mixing ratio [in wt. %] | Firing temp [° C.] | Tg [° C.] | α-value × $10^{-6}k^{-1}$ (100° C.-400° C.) | Optical appearance | Acid resistance [μg/cm²] |
|---|---|---|---|---|---|---|---|---|
| 20 | Apatite glass ceramic 9 | 1000/1 | 30 | 880 | 528 | 9.5 | very translucent | 34 |
|  | Alkali silicate glass (A) | — | 35 |  |  |  |  |  |
|  | Alkali silicate glass (B) | — | 35 |  |  |  |  |  |
| 21 | Apatite glass ceramic 14 | 1050/1 | 50 | 850 | 530 | 9.3 | milky cloudy, translucent | 38 |
|  | Alkali silicate glass (A) | — | 50 |  |  |  |  |  |
| 22 | Apatite glass ceramic 14 | 1020/1 | 50 | 870 | 542 | 8.0 | milky translucent | <100 |
|  | Alkali silicate glass (F) | — | 50 |  |  |  |  |  |
| 23 | Apatite glass ceramic 8 | 1000/1 | 40 | 910 | 552 | 8.8 | very translucent | 29 |
|  | Alkali silicate glass (C) | — | 60 |  |  |  |  |  |
| 24 | Apatite glass ceramic 1 | 1050/1 | 70 | 850 | 539 | 8.7 | slightly milky, slightly opal, translucent | 26 |
|  | Alkali silicate glass (D) | — | 30 |  |  |  |  |  |
| 25 | Apatite glass ceramic 9 | 1020/1 | 20 | 780 | 463 | 10.9 | transparent | 24 |
|  | Alkali zinc silicate glass (H) | — | 80 |  |  |  |  |  |
| 26 | Apatite glass ceramic 9 | 1020/1 | 50 | 1020 | 600 | 10.2 | very translucent, slightly brownish opal | 27 |
|  | Opalescent glass (J) | — | 50 |  |  |  |  |  |
| 27 | Apatite glass ceramic 14 | 1050/1 | 30 | 910 | 560 | 9.7 | whitish, translucent | 45 |
|  | Leucite phosphosilicate glass ceramic (G) |  | 70 |  |  |  |  |  |

Example 28

In this Example, the translucence was determined quantitatively by determining the CR value of selected dental materials according to the invention.

The British Standards Institution method of measurement was used for this purpose, which is described in the test standard for dental ceramic "BS 5612:1978".

Five specimens per material with a diameter of 20 mm and a sample thickness of 1.75 mm were fired at an appropriate sintering temperature. The specimens were ground with wet SiC powder, grain size 320, in order to obtain the desired surface quality (surface roughness Ra=0.8 μm–1.6 μm). It is important that the plane-parallelism of the opposite sides does not exceed a tolerance of ±0.01 mm since the measuring result depends to a large extent on the layer thickness. The final sample height/thickness should be 1.00±0.025 mm.

Material 2: 50 wt. % of mixture according to Example 20
50 wt. % of apatite glass ceramic according to Example 14 (heat treatment 1050° C., 1 hour)

The above results show that the translucence can be adjusted by a suitable choice of the composition of the materials.

What is claimed is:

1. A dental material comprising a chemically stable, translucent apatite glass ceramic, which contains CaO, $P_2O_5$ and F in a molar ratio of $CaO:P_2O_5:F$ 1:0.020 to 1.5:0.03 to 4.2 and comprises apatite crystals as the main crystal phase, wherein the apatite crystals are needle-shaped.

2. A dental material according to claim 1, wherein the apatite glass ceramic contains CaO, $P_2O_5$ and F in a molar ratio of $CaO:P_2O_5:F$ which is 1:0.1 to 0.5:0.1 to 1.0.

3. A dental material according to claim 1, wherein the apatite glass ceramic has a loss of mass, determined according to ISO specification 6872:1995, of less than 200 μg/cm².

4. A dental material according to claim 1, wherein the apatite glass ceramic comprises the following components:

| Component | Wt. % |
|---|---|
| SiO₂ | 45.0 to 70.0 |
| Al₂O₃ | 5.0 to 22.0 |
| P₂O₅ | 0.5 to 6.5 |
| K₂O | 3.0 to 8.5 |
| Na₂O | 4.0 to 13.0 |
| CaO | 1.5 to 11.0 |
| F | 0.1 to 2.5. |

5. A dental material according to claim 4, wherein the apatite glass ceramic further comprises at least one of the following components:

| Component | Wt. % |
|---|---|
| B₂O₃ | 0 to 8.0 |
| La₂O₃ | 0 to 5.0 |
| Li₂O | 0 to 5.0 |
| BaO | 0 to 5.0 |
| MgO | 0 to 5.0 |
| ZnO | 0 to 5.0 |
| SrO | 0 to 7.0 |
| TiO₂ | 0 to 4.0 |
| ZrO₂ | 0 to 4.0 |
| CeO₂ | 0 to 3.0. |

6. A dental material according to claim 4, wherein the apatite crystals are smaller than 35 μm in their greatest dimension.

7. A dental material according to claim 1, wherein the apatite glass ceramic has a thermal expansion coefficient of 6.0 to 12.0×10⁻⁶ K⁻¹, measured in the temperature range of from 100 to 400° C.

8. A dental material according to claim 1, wherein the apatite glass ceramic has a CR value of 0 to 0.9.

9. A dental material according to claim 1 further comprising at least one glass and/or glass ceramic of the systems selected from the group consisting of alkali silicate, alkali-alkaline earth-silicate, alkali-aluminosilicate, alkali-zinc-borosilicate, phosphosilicate and alumino-fluoro-borosilicate.

10. A dental material according to claim 1, wherein the apatite glass ceramic has a thermal expansion coefficient of 5.5 to 12.5×10⁻⁶ K⁻¹, measured in the temperature range of from 100 to 400° C.

11. A dental material according to claim 3, wherein the apatite glass ceramic has a loss mass, determined according to ISO specification 6872: 1995, of less than 100 μcm².

12. A shaped dental product, which comprises the dental material according to claim 1.

13. A shaped dental product according to claim 12, which is a dental restoration.

14. A shaped dental product according to claim 12, which comprises a core comprising ceramic or glass ceramic material and a coating applied to the core, wherein the coating comprises the apatite glass ceramic or the dental material.

15. A shaped dental product according to claim 14, wherein the glass ceramic material is a lithium disilicate glass ceramic.

16. A process for the preparation of the apatite glass ceramic according to claim 1, said process comprising a) melting a starting glass comprising the necessary components at temperatures of 1200° C. to 1650° C., b) pouring the glass melt into water to form glass granules, c) optionally comminuting the glass granules to a glass powder with an average particle size of 1 to 450 μm, based on the number of particles, and d) subjecting the glass granules or the glass powder to a treatment at temperatures of more than 900° C. and up to 1200° C. for a period of 30 minutes to 6 hours.

17. A method of coating a substrate comprising providing the substrate and coating the substrate with the dental material of claim 1.

18. The method according to claim 17, wherein the substrate is comprised of a ceramic or glass ceramic.

19. The method according to claim 18, wherein the substrate is comprised of lithium disilicate glass ceramic.

20. The method according to claim 19, wherein the lithium disilicate glass ceramic comprises:

| Component | Wt. % |
|---|---|
| SiO₂ | 57.0 to 80.0 |
| Al₂O₃ | 0 to 5.0 |
| La₂O₃ | 0.1 to 6.0 |
| MgO | 0 to 5.0 |
| ZnO | 0 to 8.0 |
| K₂O | 0 to 13.5 |
| Li₂O | 11.0 to 19.0 |
| P₂O₅ | 0 to 11.0 | with the proviso that (a) Al₂O₃+La₂O₃ is 0.1 to 7.0 wt. % and (b) MgO+ZnO is 0.1 to 9.0 wt. %.

21. The method according to claim 17, further comprising sintering the coated substrate at temperatures of 650° C. to 1050° C.

* * * * *